(12) United States Patent
da Silva Ferreira Alves et al.

(10) Patent No.: US 8,704,021 B2
(45) Date of Patent: Apr. 22, 2014

(54) PROCESS FOR INCREASING WEIGHT OF OLEFINS

(71) Applicant: UOP LLC, Des Plaines, IL (US)

(72) Inventors: Joao Jorge da Silva Ferreira Alves, Guildford (GB); James E. Rekoske, Glenview, IL (US); Christopher P. Nicholas, Evanston, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/900,853

(22) Filed: May 23, 2013

(65) Prior Publication Data

US 2013/0261359 A1    Oct. 3, 2013

Related U.S. Application Data

(62) Division of application No. 12/751,623, filed on Mar. 31, 2010, now Pat. No. 8,471,084.

(51) Int. Cl.
 *C07C 2/06* (2006.01)
 *C07C 2/64* (2006.01)
 *C07C 4/02* (2006.01)

(52) U.S. Cl.
 USPC ........... 585/323; 585/502; 585/446; 585/809; 585/648

(58) Field of Classification Search
 USPC .................. 585/323, 502, 446, 809
 See application file for complete search history.

(56) References Cited

U.S. PATENT DOCUMENTS 3,533,938 A * 10/1970 Leas ............................... 208/80

* cited by examiner

*Primary Examiner* — Thuan D Dang
(74) *Attorney, Agent, or Firm* — James C Paschall

(57) ABSTRACT

The process converts FCC olefins to heavier compounds. The heavier compounds are more easily separated from the unconverted paraffins. The heavier compounds can be recycled to an FCC unit or delivered to a separate FCC unit. Suitable conversion zones are oligomerization and aromatic alkylation zones.

5 Claims, 4 Drawing Sheets

PROCESS FOR INCREASING WEIGHT OF OLEFINS

CROSS-REFERENCE TO RELATED APPLICATION

This application is a Division of copending application Ser. No. 12/751,623 filed Mar. 31, 2010, the contents of which are hereby incorporated by reference in its entirety.

BACKGROUND OF THE INVENTION

The field of the invention is a process for converting olefins mixed with paraffins into higher molecular weight compounds for easier separation from unconverted paraffins.

Fluid catalytic cracking (FCC) is a catalytic hydrocarbon conversion process accomplished by contacting heavier hydrocarbons in a fluidized reaction zone with a catalytic particulate material. The reaction in catalytic cracking, as opposed to hydrocracking, is carried out in the absence of substantial added hydrogen or the consumption of hydrogen. As the cracking reaction proceeds substantial amounts of highly carbonaceous material referred to as coke are deposited on the catalyst to provide coked or spent catalyst. Vaporous lighter products are separated from spent catalyst in a reactor vessel. Spent catalyst may be subjected to stripping by an inert gas such as steam to strip entrained hydrocarbonaceous gases from the spent catalyst.

A high temperature regeneration with oxygen within a regeneration zone burns coke from the spent catalyst which may have been stripped. Various products may be produced from such a process, including a gasoline product and/or light product such as propylene and/or ethylene.

In such processes, a single reactor or a dual reactor can be utilized. Although additional capital costs may be incurred by using a dual reactor apparatus, one of the reactors can be operated to tailor conditions for maximizing products, such as light olefins including propylene and/or ethylene.

It can often be advantageous to maximize yield of a product in one of the reactors. Additionally, there may be a desire to maximize the production of a product from one reactor that can be recycled back to the other reactor to produce a desired product, such as propylene.

The cracking of $C_4$-$C_7$ olefins produces a high yield of propylene. The recycle of a $C_4$-$C_7$-rich stream back to an FCC reactor can be used to further increase propylene production. This recycle, however, leads to a concentration of the more refractory paraffins in the recycle stream and requires either a significant purge or a large recycle flow rate. There is no simple way of separating the olefins from the paraffins for a stream with such a wide range of boiling points.

The oligomerization of olefins over heterogeneous catalyst to heavier olefins for making motor fuels is a known technology. It is also known to alkylate olefins with paraffins over homogeneous acid catalyst to make motor fuels. Alkylation of olefins with benzene and other aromatic components typically over heterogeneous catalyst is also known for making petrochemical stock including detergent precursors.

There is need for easily separating olefins from paraffins in product streams.

SUMMARY OF THE INVENTION

In an exemplary embodiment, the present invention involves a process for converting olefins to larger compounds. $C_4$ olefins and paraffins and $C_5$-$C_7$ olefins and paraffins are passed to conversion zone to convert the $C_4$ olefins to larger molecular weight $C_4$-derived compounds and to convert the $C_5$-$C_7$ olefins to larger molecular weight $C_5$-$C_7$-derived compounds by the alkylation of $C_5$-$C_7$ olefins with aromatics. The $C_4$-derived compounds are separated from the $C_4$ olefins and paraffins, and the $C_5$-$C_7$-derived compounds are separated from $C_5$-$C_7$ olefins and paraffins. Lastly, $C_4$-derived compounds and $C_5$-$C_7$-derived compounds are fed to an FCC reactor.

In an additional exemplary embodiment, the present invention involves a process for converting olefins to larger compounds. A first stream of $C_5$-$C_7$ olefins and paraffins are passed to a first conversion zone to convert the $C_5$-$C_7$ olefins to larger molecular weight $C_5$-$C_7$-derived compounds. A second stream of $C_4$ olefins and paraffins are passed to a second conversion zone to convert the $C_4$ olefins to larger molecular weight $C_4$-derived compounds. The $C_4$-derived compounds are separated from the $C_4$ olefins and paraffins, and the $C_5$-$C_7$-derived compounds are separated from $C_5$-$C_7$ olefins and paraffins. Lastly, the $C_4$-derived compounds and the $C_5$-$C_7$-derived compounds are fed to an FCC reactor.

In a further exemplary embodiment, the present invention involves a process for converting olefins to larger compounds. A cracking catalyst is contacted with a hydrocarbon feed stream to crack hydrocarbons to cracked product hydrocarbons having lower molecular weight and deposit coke on the cracking catalyst to provide coked cracking catalyst. The coked cracking catalyst is separated from the cracked products. Coke on the coked cracking catalyst is combusted with oxygen to regenerate the cracking catalyst. The cracked products are separated in a main fractionation column. At least a portion of an overhead stream from the main fractionation column is compressed to provide a compressed overhead stream. A liquid stream is separated from the compressed overhead stream and at least a portion of the liquid stream is depropanized to provide a $C_4$-$C_7$ stream of olefins and paraffins. The stream of $C_4$-$C_7$ olefins and paraffins are fed to a conversion zone to convert the $C_4$-$C_7$ olefins to larger molecular weight $C_4$-$C_7$-derived compounds.

Additional features and advantages of the invention will be apparent from the description of the invention, the FIGURES and claims provided herein.

DEFINITIONS

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "column" means a distillation column or columns for separating one or more components of different volatilities which may have a reboiler on its bottom and a condenser on its overhead. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the outlet of the column. The bottom temperature is the liquid bottom outlet temperature. Overhead lines and bottoms lines refer to the net lines from the column downstream of the reflux or reboil to the column.

As used herein, the term "a component-rich stream" means that the rich stream coming out of a separator vessel has a greater concentration of the component than the feed to the separator vessel.

As used herein, the term "a component-lean stream" means that the lean stream coming out of a separator vessel has a smaller concentration of the component than the feed to the separator vessel.

DETAILED DESCRIPTION

We have discovered a simple way of separating the olefins from the paraffins from an FCC product stream containing $C_4$ and heavier products, preferably $C_4$-$C_7$ products and recycling the olefins either to the main FCC reactor or to a separate FCC reactor. The FCC product recovery section may have a single main fractionation column and a single gas plant. This invention includes a reaction zone in which the olefins are converted to different chemical species that make them easier to separate from the inert paraffins. The converted and separated olefin-derived product may then be recycled back to the main FCC reactor or to a separate FCC reactor.

Figure 1:
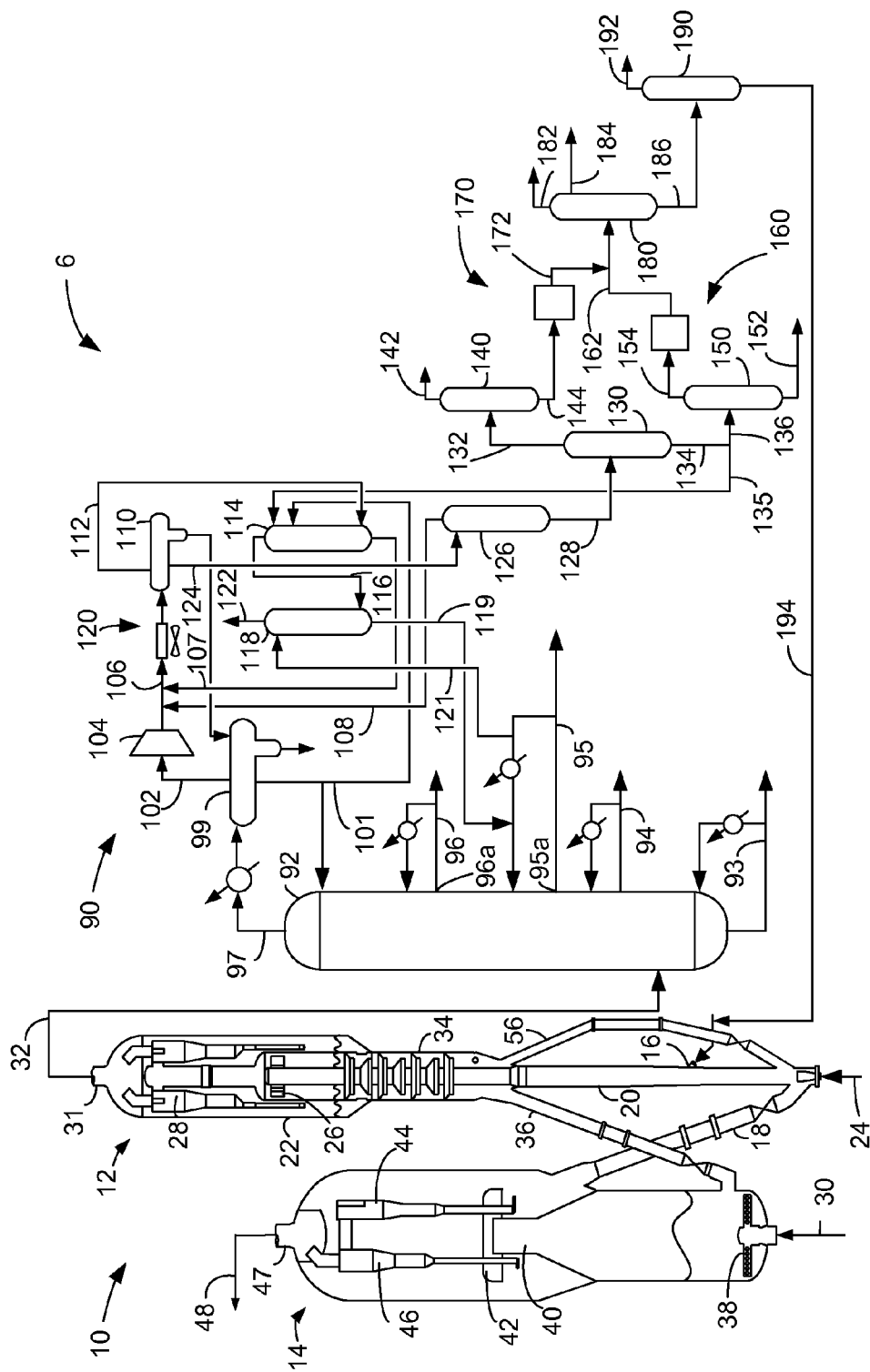
FIG. 1 is a schematic drawing of an FCC unit and an FCC product recovery section.

Now turning to FIG. 1, wherein like numerals designate like components, FIG. 1 illustrates a refinery complex 6 that generally includes an FCC unit section 10 and a product recovery section 90. The FCC unit section 10 includes a reactor 12 and a catalyst regenerator 14. Process variables typically include a cracking reaction temperature of 400° to 600° C. and a catalyst regeneration temperature of 500° to 900° C. Both the cracking and regeneration occur at an absolute pressure below 506 kPa (72.5 psia).

FIG. 1 shows a typical FCC reactor 12 in which a heavy hydrocarbon feed or raw oil stream fed by a distributor 16 is contacted with a regenerated cracking catalyst entering from a regenerated catalyst standpipe 18. This contacting may occur in a narrow riser 20, extending upwardly to the bottom of a reactor vessel 22. The contacting of feed and catalyst is fluidized by gas from a fluidizing line 24. In an embodiment, heat from the catalyst vaporizes the hydrocarbon feed or oil, and the hydrocarbon feed is thereafter cracked to lighter molecular weight hydrocarbon products in the presence of the catalyst as both are transferred up the riser 20 into the reactor vessel 22. Inevitable side reactions occur in the riser 20 leaving coke deposits on the catalyst that lower catalyst activity. The cracked light hydrocarbon products are thereafter separated from the coked cracking catalyst using cyclonic separators which may include a primary separator 26 and one or two stages of cyclones 28 in the reactor vessel 22. Gaseous, cracked products exit the reactor vessel 22 through a product outlet 31 to line 32 for transport to a downstream product recovery section 90. The spent or coked catalyst requires regeneration for further use. Coked cracking catalyst, after separation from the gaseous product hydrocarbons, falls into a stripping section 34 where steam is injected through a nozzle to purge any residual hydrocarbon vapor. After the stripping operation, the coked catalyst is carried to the catalyst regenerator 14 through a spent catalyst standpipe 36. An optional spent catalyst pipe 56 delivers spent catalyst from the stripping section 34 at a rate regulated by a control valve to the reactor riser 12 through a spent catalyst inlet.

FIG. 1 depicts a regenerator 14 known as a combustor. However, other types of regenerators are suitable. In the catalyst regenerator 14, a stream of oxygen-containing gas, such as air, is introduced through an air distributor 38 to contact the coked catalyst. Coke is combusted from the coked catalyst to provide regenerated catalyst and flue gas. The catalyst regeneration process adds a substantial amount of heat to the catalyst, providing energy to offset the endothermic cracking reactions occurring in the reactor riser 20. Catalyst and air flow upwardly together along a combustor riser 40 located within the catalyst regenerator 14 and, after regeneration, are initially separated by discharge through a disengager 42. Additional recovery of the regenerated catalyst and flue gas exiting the disengager 42 is achieved using first and second stage separator cyclones 44, 46, respectively within the catalyst regenerator 14. Catalyst separated from flue gas dispenses through diplegs from cyclones 44, 46 while flue gas relatively lighter in catalyst sequentially exits cyclones 44, 46 and exits the regenerator vessel 14 through flue gas outlet 47 in flue gas line 48. Regenerated catalyst is carried back to the riser 20 through the regenerated catalyst standpipe 18. As a result of the coke burning, the flue gas vapors exiting at the top of the catalyst regenerator 14 in line 48 contain CO, $CO_2$, $N_2$ and $H_2O$, along with smaller amounts of other species. Hot flue gas exits the regenerator 14 through the flue gas outlet 47 in a line 48 for further processing.

The FCC product recovery section 90 is in downstream communication with the product outlet 31 via line 32. In the product recovery section 90, the gaseous FCC product in line 32 is directed to a lower section of an FCC main fractionation column 92. The main fractionation column 92 is also in downstream communication with the product outlet 31. Several fractions of FCC product may be separated and taken from the main fractionation column including a heavy slurry oil from the bottoms in line 93, a heavy cycle oil stream in line 94, a light cycle oil in line 95 taken from outlet 95a and a heavy naphtha stream in line 96 taken from outlet 96a. Any or all of lines 93-96 may be cooled and pumped back to the main fractionation column 92 to cool the main fractionation column typically at a higher location. Gasoline and gaseous light hydrocarbons are removed in overhead line 97 from the main fractionation column 92 and condensed before entering a main column receiver 99. The main column receiver 99 is in downstream communication with the product outlet 31.

An aqueous stream is removed from a boot in the receiver 99. Moreover, a condensed light naphtha stream is removed in bottoms line 101 while an overhead stream is removed in line 102. A portion of line 101 is refluxed back to near a top of the main fraction column 92, so the main fractionation column 92 is in upstream communication with the main column receiver 99. The overhead stream in line 102 contains gaseous light hydrocarbon which may comprise a dilute ethylene stream. The streams in lines 101 and 102 may enter a gas recovery section 120 of the product recovery section 90.

The gas recovery section 120 is shown to be an absorption based system, but any gas recovery system may be used including a cold box system. To obtain sufficient separation of light gas components the gaseous stream in line 102 is compressed in compressor 104. More than one compressor stage may be used, and typically a dual stage compression and suitably a triple stage compression is utilized to compress the gaseous overhead stream in line 102 to between about 1.2 MPa to about 3.4 MPa (gauge) (180-500 psig) to provide a compressed first FCC product stream.

The compressed light vaporous hydrocarbon stream in line 106 may be joined by streams in lines 107 and 108, cooled and delivered to a high pressure receiver 110. An aqueous stream from the receiver 110 may be routed to the main column receiver 99. In the high pressure receiver a compressed vaporous stream in overhead line 112 is separated from a liquid stream in bottoms line 124. A gaseous hydrocarbon stream in line 112 from the overhead of the high pressure receiver 110 is routed to a lower end of a primary absorber column 114. In the primary absorber column 114, the gaseous hydrocarbon stream is contacted with an unstabilized gasoline from the main column receiver 99 in bottoms line 101 directed to an upper end of the primary absorber column 114 to effect a separation between $C_3+$ and $C_2-$ hydrocarbons. This separation is further improved by feeding stabilized gasoline from line 135 above the feed point of bottoms line 101. The primary absorber column 114 is in downstream communication with an overhead line 102 of the main column receiver via lines 106 and 112 and the bottoms line 101 of the main column receiver 99. A liquid $C_3+$ rich bottoms stream in line 107 is returned to line 106 prior to cooling. A primary off-gas stream in line 116 from the primary absorber column 114 may be directed to a lower end of a secondary absorber column 118. The secondary absorber column is in downstream communication with the primary absorber column 114. A circulating stream of light cycle oil in line 121 diverted from line 95 to an upper end of the secondary absorber column 118 absorbs most of the $C_5+$ material and some $C_3-C_4$ material. The secondary absorber column 118 is in downstream communication with the main fractionation column 92 and the primary absorber column 114. Light cycle oil from the bottom of the secondary absorber column in bottoms line 119 richer in $C_3+$ material is returned to the main fractionation column 92 via the pump-around for line 95. The main fractionation column 92 is in downstream communication with the secondary absorber column via bottoms line 119. The overhead of the secondary absorber column 118 comprising dry gas of predominantly $C_2-$ hydrocarbons with hydrogen sulfide, ammonia, carbon oxides and hydrogen is removed in a secondary off-gas stream in line 122 which can be further processed. Both of the absorber columns 114 and 118 have no condenser or reboiler, but may employ pump-around cooling circuits.

Liquid from the high pressure receiver in line 124 is sent to a stripper column 126 for fractionation. The stripper column 126 is in downstream communication with the receiver 110 via bottoms line 124. Most of the $C_2-$ is removed in the overhead of the stripper column 126 and returned to line 106 via overhead line 108. In an aspect, a liquid bottoms stream from the stripper column 126 is sent to a process fractionation column 130 via line 128. The stripper column 126 has no condenser but receives cooled liquid feed in line 124.

The process fractionation column 130 separates a $C_3$-rich overhead stream in line 132 from a $C_5$-, $C_6$- and/or $C_7$-rich bottoms stream in a bottoms line 134. The overhead stream in overhead line 132 from the process fractionation column 130 may comprise $C_3$ olefins and paraffins and preferably comprises $C_3$ and $C_4$ olefins and paraffins. A bottoms stream in the bottoms line 134 may comprise $C_5$ olefins and paraffins and preferably comprises $C_5$, $C_6$ and/or $C_7$ olefins and paraffins designated hereinafter as $C_5-C_7$ olefins and paraffins. The bottoms stream in line 134 may also contain $C_5+$ naphthenes and $C_6+$ aromatics as well as heavier naphtha components.

It is desired to send $C_4-C_7$ olefins to an FCC reactor 12 or a separate FCC reactor, not shown, to further produce light olefins. However, recycling a $C_4-C_7$ stream of paraffins and olefins to FCC reactor 12 will result in the build-up of inert paraffins. Separating the paraffins from the olefins for all of the carbon numbers in the naphtha range would be difficult. The present invention proposes to convert the olefins to heavier compounds, so they can be easily separated from the unconverted, lighter paraffins.

In an embodiment, the mixed stream of $C_3$ and/or $C_4$ olefins and paraffins in overhead line 132 may be delivered to an LPG splitter column 140. The LPG splitter column 140 is in downstream communication with the overhead line 132 of the process fractionation column 130. A stream of $C_3$ olefins and paraffins separated in overhead line 142 of the LPG splitter column 140 may be further treated to recover propylene. A bottoms stream of $C_4$ olefins and paraffins may be separated in a bottoms line 144.

A portion of the stabilized gasoline in bottoms line 134 may be recycled in line 135 to a top of the primary absorber column above the inlet point of line 101 and 112 to improve the recovery of $C_3+$. In an embodiment, a net bottoms stream 136 from the debutanizer column may be fractionated in a naphtha splitter column 150. A $C_6+$, $C_7+$ or more preferably $C_8+$ heavy naphtha stream, may be recovered in a bottoms line 152 for further processing and/or storage. An overhead stream comprising $C_5$, $C_5-C_6$ or more preferably $C_5-C_7$ olefins and paraffins as well as naphthenes and aromatics is provided in line 154.

In an embodiment, the overhead stream 154 comprising $C_5-C_7$ olefins and paraffins may be fed to a first conversion zone 160 that may comprise a $C_5-C_7$ conversion zone which is in downstream communication with the overhead line 154 of the naphtha splitter column 150 and the bottoms line 134 of the process fractionation column 130. Any, some or all of $C_5-C_7$ olefins may be converted in the first conversion zone to larger molecular weight $C_5-C_7$-derived compounds. Suitable reactions that may be conducted in the first conversion zone 160 may include oligomerization and aromatic alkylation. A first product that may comprise a $C_5-C_7$-derived product exits the first conversion zone in line 162.

The bottoms stream of $C_4$ olefins and paraffins in bottoms line 144 may be delivered to a second conversion zone 170 which is in downstream communication with the bottoms line 144 of the LPG splitter column 140 and an overhead line 132 of the process fractionation column 130. The second conversion zone may be a $C_4$ conversion zone. $C_4$ olefins may be converted in the second conversion zone to larger molecular weight $C_4$-derived compounds. Suitable reactions that may be conducted in the second conversion zone 170 include oligomerization and aromatic alkylation. A second product that may comprise a $C_4$-derived product exits the second conversion zone in line 172. The same process or different processes can be conducted in each of the first and the second conversion zones 160 and 170. In FIG. 1, the first conversion effluent in line 162 is joined by the second conversion effluent in line 172 and enters a stabilizer column 180. The two lines 162 and 172 may enter the stabilizer column 180 separately or jointly. Additionally, the stream in line 172 may be cooled and separated, in which case the vapor may enter the column 180 above the liquid feed which may or may not enter with line 162. The stabilizer column 180 may be in downstream communication with first and second conversion zones 160 and 170.

Three streams may be fractionated and removed from the stabilizer column 180. An overhead gas stream in line 182 comprising $C_3-$ materials which may be recovered, enter the gas plant or be sent to fuel gas. A side cut stream of $C_4$ paraffins in line 184 may be recovered or further processed in an LPG treatment section or in an oligomerization zone as explained hereinafter. A bottoms stream in line 186 comprising heavier $C_4$ and $C_5$-$C_7$ derived compounds may be forwarded to a product splitter column 190.

The product splitter column is in downstream communication with the first and second conversion zones 160 and 170, respectively, which may be oligomerization or alkylation reactors, and a bottoms line 186 from the stabilizer column 180. Alternatively, line 162 may not enter the stabilizer column 180 but bypass it to the product splitter column 190 in which case line 172 enters the stabilizer column separately. The product splitter column may provide two streams. An overhead stream comprising $C_5$-$C_7$ unconverted materials in line 192 which may be recovered for further processing such as in a naphtha hydrotreater to remove sulfur in route to the gasoline pool or for use in an alkylation zone as described hereinafter. A portion or all of the bottoms stream in line 194 comprising $C_4$ and $C_5$-$C_7$ derived compounds of higher molecular weight such as alkylaromatics or oligomers may be recycled as feed to the FCC reactor 12. FIG. 1 shows the recycle stream in line 194 entering with the primary feed in line 16, but it may enter the riser 20 at a different location. According to an aspect, the FCC reactor 12 is in downstream communication with a bottoms line 194 of the product splitter column 190. The bottoms fraction in line 194 may be returned to the FCC reactor 12 or a different FCC reactor for additional cracking to increase yield of light olefins.

Figure 2:
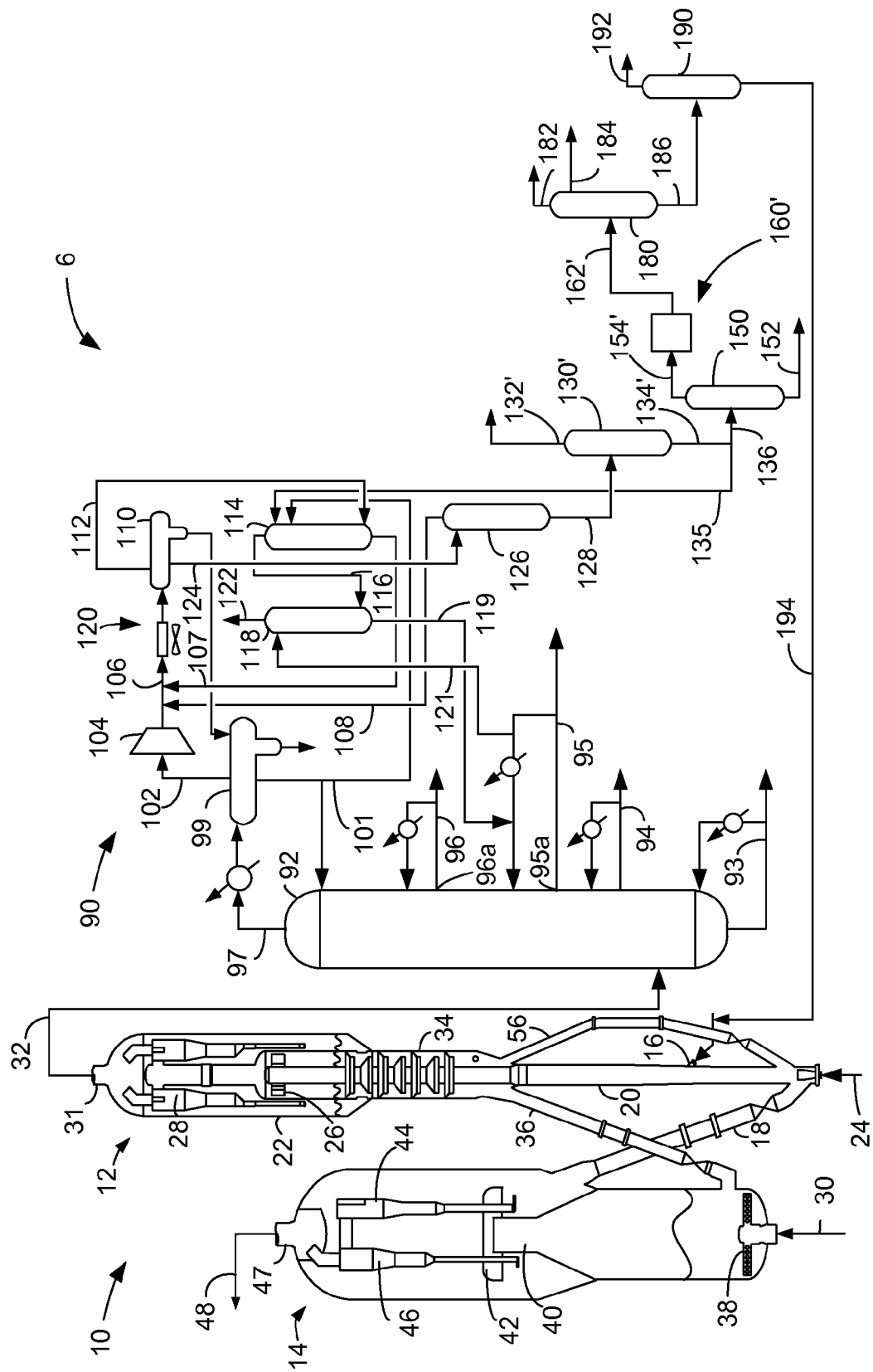
FIG. 2 is an alternative schematic drawing of an FCC unit and an FCC product recovery section.

FIG. 2 shows this alternative embodiment to FIG. 1. Only one conversion zone 160' is shown in FIG. 2. Elements in FIG. 2 that correspond to elements in but are different from FIG. 1 are indicated by a reference numeral with a prime sign ('). All other items in FIG. 2 are the same as in FIG. 1.

In an aspect, a liquid bottoms stream in line 128 from the stripper column 126 which comprises a portion of the liquid stream in bottoms line 124 is sent to a process fractionation column 130'. The process fractionation column 130' may be in downstream communication with the stripping column 126 via bottoms line 128. The process fractionation column 130' may comprise a depropanizer column that separates a $C_3$-rich overhead stream in line 132 from a $C_4$-rich and/or a $C_5$-rich bottoms stream in line 134'. The overhead stream in line 132' from the process fractionation column may comprise $C_3$ product comprising olefins and paraffins while a bottoms stream in line 134' comprises $C_4$, $C_5$, $C_6$ and/or $C_7$, hereinafter referred to as a $C_4$-$C_7$ stream comprising olefins and paraffins. The bottoms stream in line 134' may also contain $C_5$+ naphthenes and $C_6$+ aromatics as well as heavier naphtha components.

A portion of the naphtha in bottoms line 134' may be recycled in line 135 to a top of the primary absorber column above the inlet point of line 101 and 112 to improve the recovery of $C_3$+. In an embodiment, a net bottoms stream 136 from the depropanizer column may be fractionated in a naphtha splitter column 150. A $C_5$+, $C_6$+, $C_7$+ or preferably a $C_8$+ heavy naphtha stream, is recovered in a bottoms line 152 for further processing and/or storage. An overhead stream comprising $C_4$, $C_4$-$C_5$, $C_4$-$C_6$ or more preferably $C_4$-$C_7$ olefins and paraffins as well as naphthenes and aromatics is provided in line 154'.

In an embodiment, the overhead stream 154' may be fed to a first conversion zone 160' that may comprise a $C_4$-$C_7$ conversion zone which is in downstream communication with the bottoms line 134' of the process fractionation column 130'. Any, some or all of $C_4$-$C_7$ olefins may be converted in the first conversion zone to larger molecular weight $C_4$-$C_7$-derived compounds. Suitable reactions that may be conducted in the first conversion zone 160' may include oligomerization and aromatic alkylation. A first product that may comprise a $C_4$-$C_7$-derived product exits the first conversion zone in line 162' and enters the stabilizer column 180 and may be processed as in FIG. 1 to forward $C_4$-$C_7$-derived products to an FCC reactor.

Figure 3:
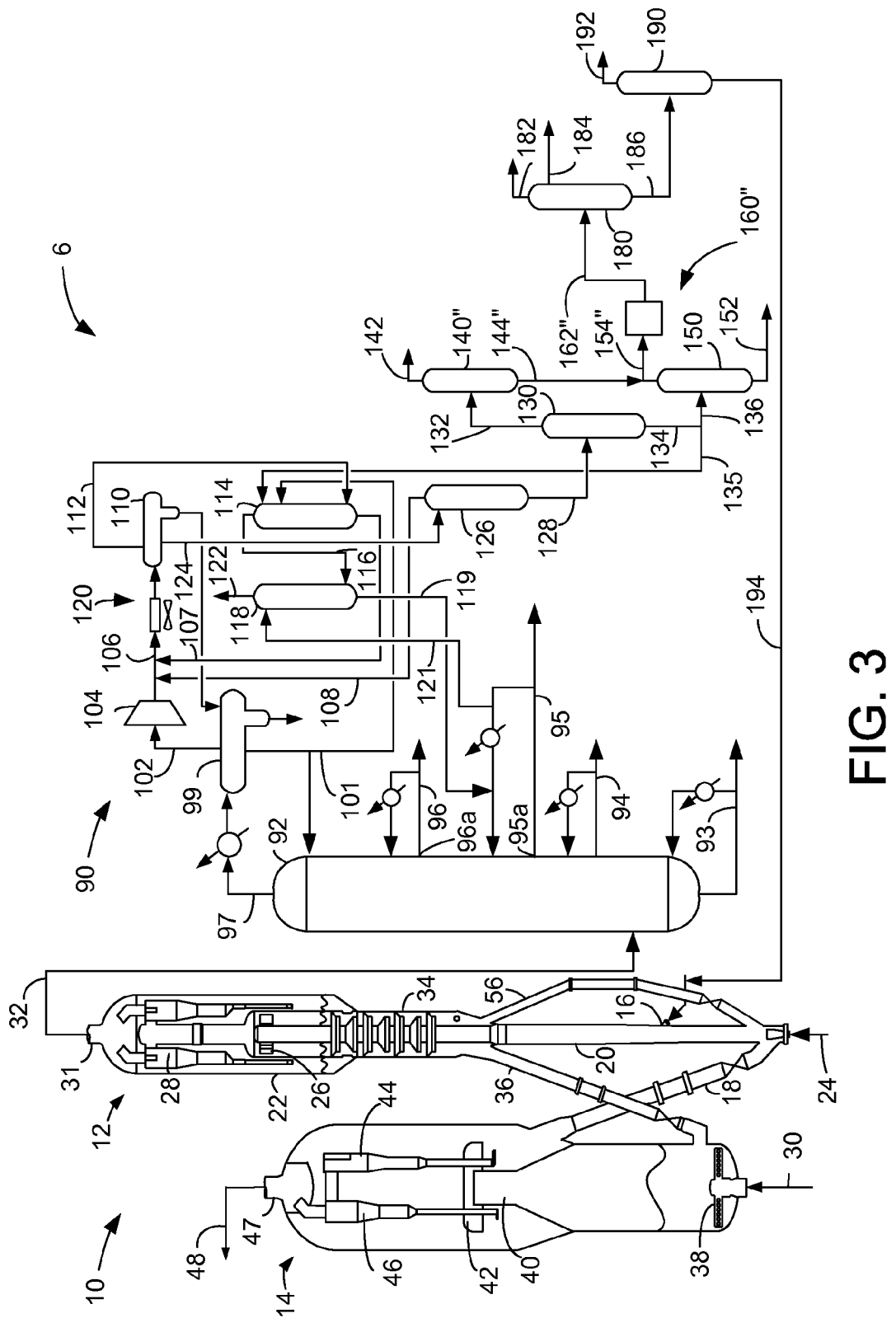
FIG. 3 is a further alternative schematic drawing of an FCC unit and an FCC product recovery section.

FIG. 3 shows an alternative embodiment to FIGS. 1 and 2. Only one conversion zone 160" is shown in FIG. 3. Elements in FIG. 3 that correspond to elements in but are different from FIG. 1 are indicated by a reference numeral with a double prime sign ("). All other items in FIG. 3 are the same as in FIG. 1.

The bottoms stream of $C_4$ olefins and paraffins in bottoms line 144" may be delivered to a first conversion zone 160" which is in downstream communication with the bottoms line 144" of the LPG splitter column 140", an overhead line 132 of the process fractionation column 130, a bottoms line 134 of the process fractionation column 130 and an overhead line 154" of the naphtha splitter column 150. The bottoms line 144" may join overhead line 154" or enter the first conversion zone 160" separately.

The first conversion zone 160" may comprise a $C_4$-$C_7$ conversion zone in which any, some or all of $C_4$-$C_7$ olefins may be converted in the first conversion zone to larger molecular weight $C_4$-$C_7$-derived compounds. Suitable reactions that may be conducted in the first conversion zone 160" may include oligomerization and aromatic alkylation. A first product that may comprise a $C_4$-$C_7$-derived product exits the first conversion zone in line 162" and enters the stabilizer column 180 and may be processed as in FIG. 1 to forward $C_4$-$C_7$-derived products to an FCC reactor.

Figure 4:
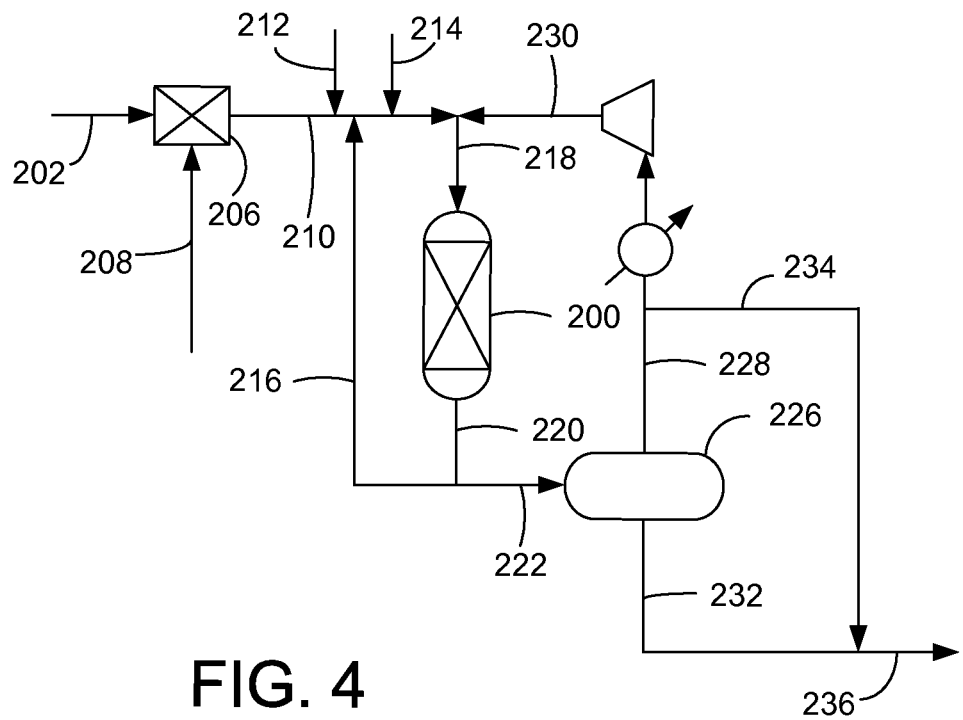
FIG. 4 is a schematic of an oligomerization conversion zone.

The first and/or the second conversion zone may comprise an oligomerization reactor 200 which is exemplified in FIG. 4. The oligomerization reactor 200 may be in downstream communication with the bottoms line 144, 144" of an LPG splitter column 140 of FIGS. 1 and 3. The same or a separate oligomerization reactor 200 may be in downstream communication with the bottoms line 134, 134' from process fractionation column 130, 130' and/or the overhead line 154, 154' of the naphtha splitter column 150 of FIGS. 1 and 2. In an embodiment, diolefins in the bottoms stream in line 144, 144", 154 or 154' may be delivered in line 202 to be first reacted with a selective hydrogenation catalyst in selective hydrogenation zone 206, to selectively saturate diolefins without completely saturating them to paraffins. Suitable conditions for operation of a selective hydrogenation process are described, for example, in U.S. Pat. No. 6,166,279 and U.S. Pat. No. 6,075,173. Such conditions include passing the olefin and paraffin stream in line 202 in the liquid phase and hydrogen from line 208 at molar ratio 0.5 to 5 moles hydrogen per mole of diolefin over a catalyst comprising at least one metal selected from the group formed by nickel, palladium and platinum, deposited on a support such as aluminum oxide, at a temperature of 20° to 200° C. (68° to 392° F.), a pressure of 689 to 3447 kPa(g) (100 to 500 psig), and a space velocity of 0.5 to 10 $hr^{-1}$. Two or more reaction zones may be used although only one is shown. Each reaction zone may employ a recycle (not shown) of reactor effluent to the reactor inlet with a ratio of recycle to fresh olefinic feed stream ranging from 0 to 20. The residual diolefin content of such a process can be in the range 1 to 100 wppm, depending on the severity of the operation.

The effluent from the selective hydrogenation reactor in line 210 with a diolefin concentration that is less than in line 202 may be mixed with none, one, some or all of a paraffinic diluent in line 212 which may be a portion of the paraffinic stream in line 184 of FIG. 1 or 2, a selectivity modifier in line 214 and an effluent recycle stream in line 216 and is then fed to a oligomerization reactor 200 in line 218. In the oligomerization reactor 200, $C_4$ olefins from line 144, $C_5$-$C_7$ olefins from line 154 or $C_4$-$C_7$ olefins from line 154' or 154" are contacted with an oligomerization catalyst at oligomerization conditions to oligomerize the olefins to produce heavier olefins. The oligomerization reactor is shown as a downflow reactor, but an upflow reactor may also be suitable.

Conditions for the operation of an oligomerization process include passing the olefinic liquid over a fixed bed of catalyst such as SPA or a sulfonic acid ion exchange resin such as Amberlyst A-15, A-35, A-16, A-36, Dowex 50 or the like. Several means can be used to restrict the formation of higher oligomers. These include addition of a paraffinic diluent in line 212 to the oligomerization reactor when SPA catalyst is used, recycle of a portion of the oligomerization reactor effluent in line 216 to the oligomerization reactor 200 and addition of 0.1 to 3.0 wt-% oxygenated selectivity modifier in line 214 to the oligomerization reactor when resin catalyst is used. Avoiding heavy olefin production is not critical. Hence, one or all of the streams in lines 212-216 may be omitted.

The preferred operating conditions applicable when an SPA catalyst is used differ from those when an ion exchange resin catalyst is used. Preferred temperatures for operation with an SPA catalyst are in the range 40° to 260° C., and more typically in the range 75° to 230° C., while preferred temperatures for operation with an ion-exchange resin catalyst are in the temperature range 0° to 200° C., and more typically in the range 40° to 150° C. Preferred pressures for operation with an SPA catalyst are in the range 689 to 8274 kPa(g) (100 to 1200 psig), and more typically in the range 1379 to 6895 kPa(g) (200 to 1000 psig), while preferred pressures for operation with an ionic resin catalyst are in the range 345 to 3447 kPa(g) (50 to 500 psig), and more typically in the range 1379 to 2413 kPa(g) (200 to 350 psig). These pressures may be kept in the lower end of the range, so an additional compressor is not required to boost the pressure above the system pressure needed for the selective hydrotreating reactor 206. A preferred space velocity range for operation with SPA catalyst is about 0.5 to about 5 $hr^{-1}$ and for operation with an ion-exchange resin catalyst is 0.3 to 20 $hr^{-1}$ depending on the properties of the oligomerization reactor feed such as olefin content and type. Other catalysts may be suitable.

An oligomerization reactor product is withdrawn from oligomerization reactor 200 through effluent line 220. A portion of the oligomerization reactor effluent may be recycled to the oligomerization reactor through recycle line 216 to control the exotherm. A second portion of the oligomerization reactor product is passed through process line 222 to a flash drum 226, in which an unreacted vapor stream and an oligomerization product-rich liquid stream are provided. The unreacted vapor stream leaves flash drum 226 in vapor line 228 for further processing. A portion of vapor stream in line 228 may be recycled by line 230 to the oligomerization reactor 200 after condensing and compression. The oligomerization-rich product stream in line 232 is removed from a bottom of the flash drum 226. A purge in line 234 to remove paraffins from the unreacted vapor stream in line 228 joins line 232 to provide line 236 which becomes line 162. 162' or 172.

Figure 5:
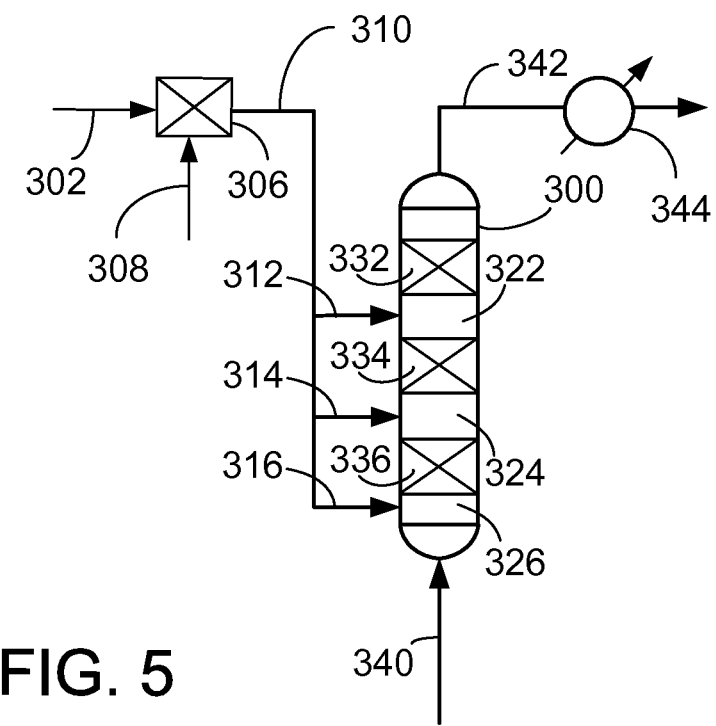
FIG. 5 is an alternative schematic of an aromatic alkylation conversion zone.

In another embodiment, the first and/or second conversion zone may be an aromatic alkylation reactor 300 as exemplified in FIG. 5. The aromatic alkylation reactor 300 may be in downstream communication with the bottoms line 144, 144" of an LPG splitter column 140 of FIGS. 1 and 3. The same or a separate aromatic alkylation reactor 300 may be in downstream communication with the bottoms line 134, 134' from the process fractionation column 130, 130' and/or the overhead line 154, 154' of the naphtha splitter column 150 of FIGS. 1 and 2. In an embodiment, diolefins in the bottoms stream in line 144, 144" or overhead line 154, 154' may be delivered in line 302 to be first reacted with a selective hydrogenation catalyst in selective hydrogenation zone 306, to selectively saturate diolefins without completely saturating them to paraffins. Suitable conditions for operation of a selective hydrogenation process are described with respect to FIG. 4. Hydrogen is passed from line 308 into the reactor 306.

A stream comprising olefins and paraffins from selective hydrogenation reactor 306 in line 310 is injected into an alkylation reactor 300. In an aspect, a drier (not shown) on line 310 may be used to remove water to low concentrations which could affect the catalyst. Other guard beds are also contemplated to remove catalyst poisons. Although transalkylation reactions occur in the alkylation reactor 300, alkylation reactions are predominant. The alkylation reactor is shown as an upflow reactor with respect to the aromatic stream, but a downflow reactor may also be suitable. The stream in line 310 of olefins and paraffins is injected into the alkylation reactor 300 in several lines 312, 314 and 316 into pre-bed spaces 322, 324 and 326 prior to entry into catalyst beds 332, 334 and 336, respectively. The catalyst beds 332, 334 and 336 contain alkylation catalyst to alkylate aromatics and olefins to produce alkylbenzenes. An aromatic feed stream in a line 340 is fed to the alkylation reactor 300 where it initially mixes with olefins and paraffins from the line 316 in the pre-bed space 326 and together enter the catalyst bed 336. The aromatic feed stream in line 340 may be in downstream communication with line 192 of FIG. 1, 2 or 3 or may come at least in part from an external stream derived from pyrolysis gasoline from a steam cracking unit preferably after hydrotreating. Other aromatic stream sources are contemplated.

The effluent from the catalyst bed 336 is mixed with fresh olefins and paraffins from the line 314 in the pre-bed space 324 and together enter into the catalyst bed 334. The effluent from the catalyst bed 334 is mixed with fresh olefins and paraffins from the line 312 in the pre-bed space 322 and together enter into the catalyst bed 332. The process is repeated for the number of beds in the alkylation reactor 300. Although three catalyst beds are shown in the alkylation reactor 300, more or less beds and additional reactors may be suitable. Alkylation effluent from the alkylation reactor 300 is transported in an effluent line 342. A heat exchanger 344 may cool the effluent in the line 342 to a desirable temperature. The alkylation reactor effluent stream may be depressurized by passing through a pressure control valve or pressurized by passing through a pump, both of which are not shown. Effluent line 342 carrying alkylation product and unreacted paraffins becomes line 162, 162', 162" or 172

Benzene is by far the most important representative of the alkylatable aromatic compounds which may be used as an alkylation substrate in line 340. An aromatic feed stream may comprise from about 5 to 99.9 mol-% benzene. More generally the aromatic compounds may be selected from the group consisting of benzene, naphthalene, anthracene, phenanthrene, and substituted derivatives thereof. The most important class of substituents found on the aromatic nucleus of alkylatable aromatic compounds are mono- or poly-alkyl moieties containing from 1 up to about 20 carbon atoms. Other important substituents are the hydroxyl moiety and the alkoxy moiety whose alkyl group also contains from 1 up to 20 carbon atoms.

A wide variety of catalysts can be used in the alkylation reaction zone. The preferred catalyst for use in this invention is a zeolitic catalyst. The catalyst of this invention will usually be used in combination with a refractory inorganic oxide binder. Preferred binders are alumina or silica. Suitable zeolites include zeolite beta, ZSM-5, PSH-3, MCM-22, MCM-36, MCM-49, and MCM-56. Zeolite beta is described in U.S. Pat. No. 5,723,710. A preferred alkylation catalyst is UZM-8. Catalysts with FAU structures are suitable. The zeolite will be present in an amount of at least 50 wt-% of the catalyst and more preferably in an amount of at least 60 wt-% of the catalyst. However, if the zeolite is provided on a layered sphere or on an enhanced surface, much less zeolite concentration may be necessary.

The particular conditions under which the alkylation reaction is conducted depends upon the aromatic compound and the olefin used. Since the reaction is conducted under at least partial liquid phase conditions, reaction pressure may be adjusted to maintain the olefin at least partially in the liquid phase. Olefin feed in the gas phase may also be suitable. For higher olefins the reaction may be conducted at autogenous pressure. Pressures can vary within a wide range of about 101 to about 13172 kPa (gauge) (1 to 1900 psig). As a practical matter the pressure normally is in the range between about 1379 and about 6985 kPa (gauge) (200 to 1000 psig) but usually is in a range between about 2069 and 4137 kPa (gauge) (300 and 600 psig). The temperature range appropriate for alkylation of the alkylatable aromatic compounds with the olefins in the $C_4$-$C_7$ range is between about 60° and about 400° C., with the most usual temperature range being between about 90° and 250° C. Reactants generally pass through the alkylation zone at a mass flow rate sufficient to yield a liquid hourly space velocity from 0.2 to 50 $hr^{-1}$ and especially from about 0.5 to 10 $hr^{-1}$. The ratio of alkylatable aromatic compound to olefin should be between about 1:1 and as high as about 20:1, with a ratio of 2.0 to 1.0 being preferred.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for converting olefins to larger compounds comprising:
    passing $C_4$ olefins and paraffins and $C_5$-$C_7$ olefins and paraffins to conversion zone to convert the $C_4$ olefins to larger molecular weight C4-derived compounds and to convert the $C_5$-$C_7$ olefins to larger molecular weight $C_5$-$C_7$-derived compounds by the alkylation of $C_5$-$C_7$ olefins with aromatics;
    separating the $C_4$-derived compounds from the $C_4$ olefins and paraffins;
    separating the $C_5$-$C_7$-derived compounds from $C_5$-$C_7$ olefins and paraffins; and
    feeding $C_4$-derived compounds and $C_5$-$C_7$-derived compounds to an FCC reactor.

2. The process of claim 1, wherein said $C_4$ olefins and paraffins and said $C_5$-$C_7$ olefins and paraffins are passed to the same conversion zone.

3. The process of claim 1, wherein said $C_4$ olefins and paraffins and said $C_5$-$C_7$ olefins and paraffins are passed to different conversion zones.

4. The process of claim 3, wherein a first conversion zone to which said $C_4$ olefins and paraffins are passed is an oligomerization zone.

5. The process of claim 3, wherein a first conversion zone to which said $C_4$ olefins and paraffins are passed is an aromatic alkylation zone.

* * * * *